(12) United States Patent
Langlotz

(10) Patent No.: US 11,794,990 B2
(45) Date of Patent: Oct. 24, 2023

(54) VOMIT BAG WITH ANTI-NAUSEA AROMA DISPENSER

(71) Applicant: Bennet K. Langlotz, Dallas, TX (US)

(72) Inventor: Bennet K. Langlotz, Dallas, TX (US)

(*) Notice: Subject to any disclaimer, the term of this patent is extended or adjusted under 35 U.S.C. 154(b) by 175 days.

(21) Appl. No.: 17/189,393

(22) Filed: Mar. 2, 2021

(65) Prior Publication Data
US 2021/0179348 A1 Jun. 17, 2021

Related U.S. Application Data

(63) Continuation of application No. 15/262,095, filed on Sep. 12, 2016, now abandoned.

(51) Int. Cl.
| | | |
|---|---|---|
| B65F 1/00 | (2006.01) | |
| A61M 21/02 | (2006.01) | |
| A61M 21/00 | (2006.01) | |

(52) U.S. Cl.
CPC ........... *B65F 1/0026* (2013.01); *A61M 21/02* (2013.01); *A61M 2021/0016* (2013.01); *B65F 2210/129* (2013.01); *B65F 2220/106* (2013.01); *B65F 2240/172* (2013.01); *B65F 2250/108* (2013.01); *B65F 2250/11* (2013.01); *B65F 2250/114* (2013.01)

(58) Field of Classification Search
CPC .............. B65F 1/0026; B65F 2210/129; B65F 2220/106; B65F 2240/172; B65F 2250/108; B65F 2250/11; B65F 2250/114; A61M 21/02; A61M 2021/0016; A61M 2205/583; A61M 15/08; A61M 21/00; A61J 19/00
See application file for complete search history.

(56) References Cited

U.S. PATENT DOCUMENTS

| | | | | |
|---|---|---|---|---|
| 6,554,151 | B1 * | 4/2003 | Brennan | B65F 1/06 220/495.04 |
| 2008/0154219 | A1 * | 6/2008 | Longo | A61J 19/00 604/327 |
| 2009/0067760 | A1 * | 3/2009 | Shelley | B65D 81/28 264/238 |
| 2011/0180008 | A1 * | 7/2011 | Davis | B65F 1/0006 422/5 |
| 2016/0158114 | A1 * | 6/2016 | Barry | A61J 19/00 206/204 |
| 2017/0305662 | A1 * | 10/2017 | Bolos | B65F 1/062 |

* cited by examiner

*Primary Examiner* — Erich G Herbermann
*Assistant Examiner* — Alessandro R Del Priore
(74) *Attorney, Agent, or Firm* — Bennet K. Langlotz; Langlotz Patent & Trademark Works, LLC

(57) ABSTRACT

A vomit receptacle that includes a nausea relief substance that may be released on demand to relieve the nausea of a user who also must be prepared to contain a vomiting event. The receptacle may be a flexible bag, and the relief substance may be contained in a sealed packet in the bag, or in a kit with the bag. The substance may be an aromatic essential oil such as peppermint oil.

16 Claims, 3 Drawing Sheets

VOMIT BAG WITH ANTI-NAUSEA AROMA DISPENSER

CROSS-REFERENCE TO RELATED APPLICATION

This application is a Continuation of U.S. patent application Ser. No. 15/262,095 filed on Sep. 12, 2016, entitled "Vomit Bag with Anti-nausea Aroma Dispenser," which is hereby incorporated by reference in its entirety for all that is taught and disclosed therein.

FIELD OF THE INVENTION

This invention relates to disposable waste receptacles known as "barf bags" and the treatment of nausea.

BACKGROUND OF THE INVENTION

Vomit bags are disposable receptacles used for receiving and containing vomit in a range of environments, including vehicles, aircraft, homes, ships, and hospitals. Vomiting events often occur in response to conditions that trigger nausea, such as motion, medications, illness, food poisoning, and pregnancy.

Some vomiting events are preventable in many mild cases. If given a little extra time for a wave of nausea to pass, or to change the conditions that may be causing motion sickness (like reading as a car passenger) the sufferer may entirely avoid the need to vomit.

One effective means to ease mild nausea and often avoid vomiting is by inhaling certain aromatic compounds such as peppermint oil. Such compounds are often available as essential oils and include Peppermint, Ginger, Lavender, Roman chamomile, Cardamom, Coriander, Fennel, Nutmeg, Melissa, Aniseed, Star anise, Bergamot, Black pepper, Lemon, Spearmint, Grapefruit, Geranium, among many others. Any scents that relieve or reduce nausea are defined as "nice" for the purposes of this application. However, these are not generally available at the time of immediate need, or in places where vomit bags are generally provided.

An additional problem is that the use of aromatic compounds to relieve nausea can be subject to error, and a misapplication of oil from a kit of oils can worsen the nausea or other conditions. For instance, one suffering from nausea during late pregnancy must avoid certain oils that may be found in selection of aromatic oils and dangerously confused with a nausea-reducing oil such as peppermint.

Therefore, there is a need for a vomit receptacle that includes a nausea relief substance that may be released on demand to relieve the nausea of a user who also must be prepared to contain a vomiting event. The receptacle may be a flexible bag, and the relief substance may be contained in a sealed packet in the bag, or in a kit with the bag. The substance may be an aromatic essential oil such as peppermint oil.

DESCRIPTION OF THE CURRENT EMBODIMENT

Figure 1:
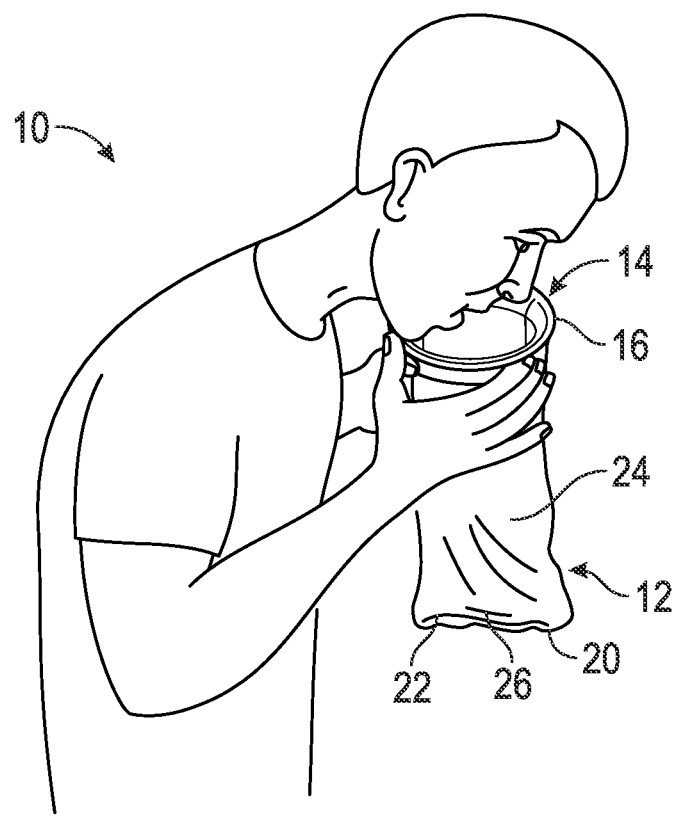
FIG. 1 is a view of a preferred embodiment of the invention in a deployed condition in use.

FIG. 1 shows a nauseous user 10 employing a vomit bag or "barf bag" according to a preferred embodiment of the invention. The bag may be sealed paper, foil, rubber, or any flexible, thin material but in the preferred embodiment it is plastic, like typical vomit bags used by hospitals and in other medical applications. The bag has an open top end 14 with a circular stiffener ring 16 encircling the opening. The bag is an elongated tube with a closed lower end 20 that may have a bottom stiffener panel 22. The bag defines an interior space 24 that is open only at the top end, where the user may place his nose or mouth.

Attached to the bottom of the bag inside the space is an aromatic carrier 26. The carrier contains an aromatic substance that has a "nice" aroma that tends to relieve nausea and prevent vomiting. This is peppermint oil in the preferred embodiment, but may be any of a wide range of other carriers of this scent, or of numerous other scents that tend to relieve nausea. In use, the substance is open to the air in the bag, and diffuses through the air to the user's nose, while remaining relatively contained and concentrated in the bag for a beneficial effect with a limited amount of the substance.

Figure 2:
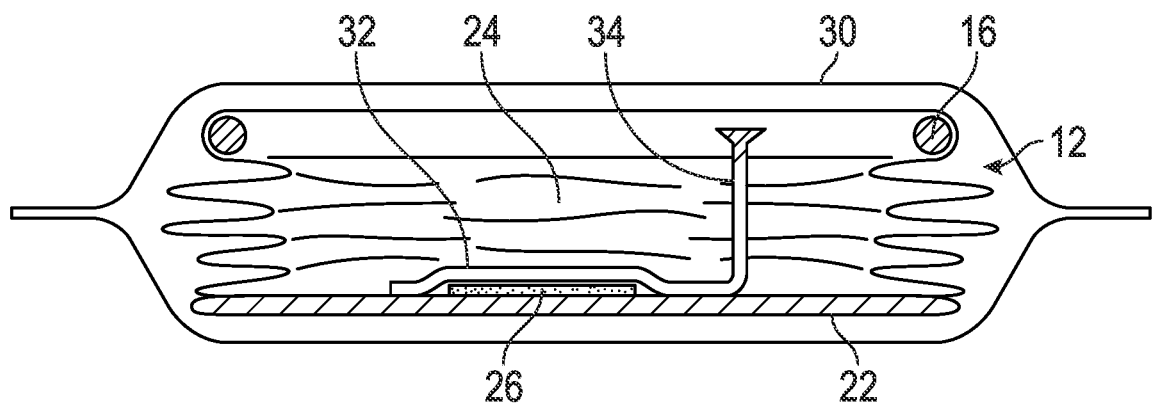
FIG. 2. is a side sectional view of the embodiment of FIG. 1 in a stored condition.
Figure 3:
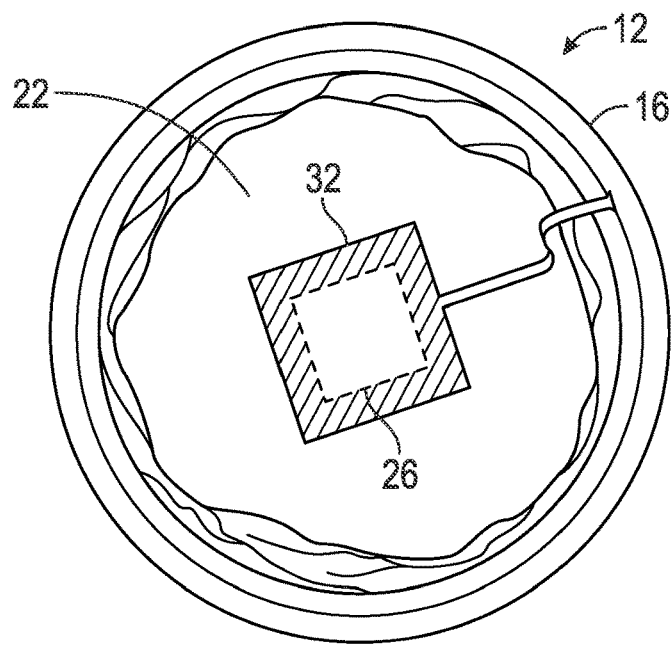
FIG. 3 is a top view of the embodiment of FIG. 1.

FIGS. 2 and 3 show the bag 12 and carrier 26 in a compact stored condition, in this case in an outer sealed pouch 30 formed of transparent plastic such as cellophane. This maintains the bag in a sanitary or sterile condition when in storage, and assures a user that the bag has not been used by others. It also helps to contain any odors that may escape the carrier. In this embodiment, the carrier 26 is an absorbent pad of fibrous material that is adhered to the bottom of the bag on the bottom panel 22, and a cover panel 32 covers and encloses the carrier to preserve and contain the aromatic substance that saturates or moistens or is otherwise carried by the carrier. In alternative embodiments, the carrier may be contained in a packet or envelope such as are used for wet wipes or magazine perfume samples, and this packet can be adhered to the bottom of the bag.

Figure 4:
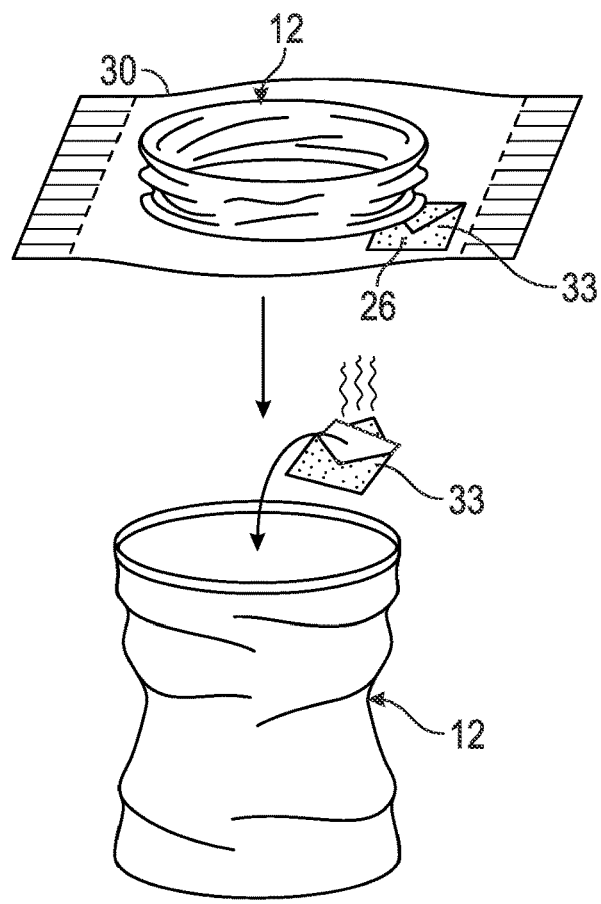
FIG. 4 is a side view sequence of an alternative embodiment of the invention is a stored condition and a ready-for-use condition.

In alternative embodiments such as shown in FIG. 4, the packet 33 may be detached from the bag, and tossed into the bag after tearing open the packet and releasing its aroma. Preferably, a detached packet is contained with the bag in the pouch as a kit that ensures that the therapeutic aroma source will be readily available to a user.

To unseal the sealed packet and let the aroma escape to be smelled by the user, a tag 34 extending from the packet is attached at its far end to the top ring 16 of the bag. Thus when the bag is extended to full length, the tag is pulled by the action to remove the cover panel, or tear the packet. In alternative embodiments such as shown in FIG. 5, the tag may simply be a tab 36 that is manually pulled by the user, and the packet may be left sealed with the tab unpulled by users not desiring to smell the aromatic substance.

Figure 5:
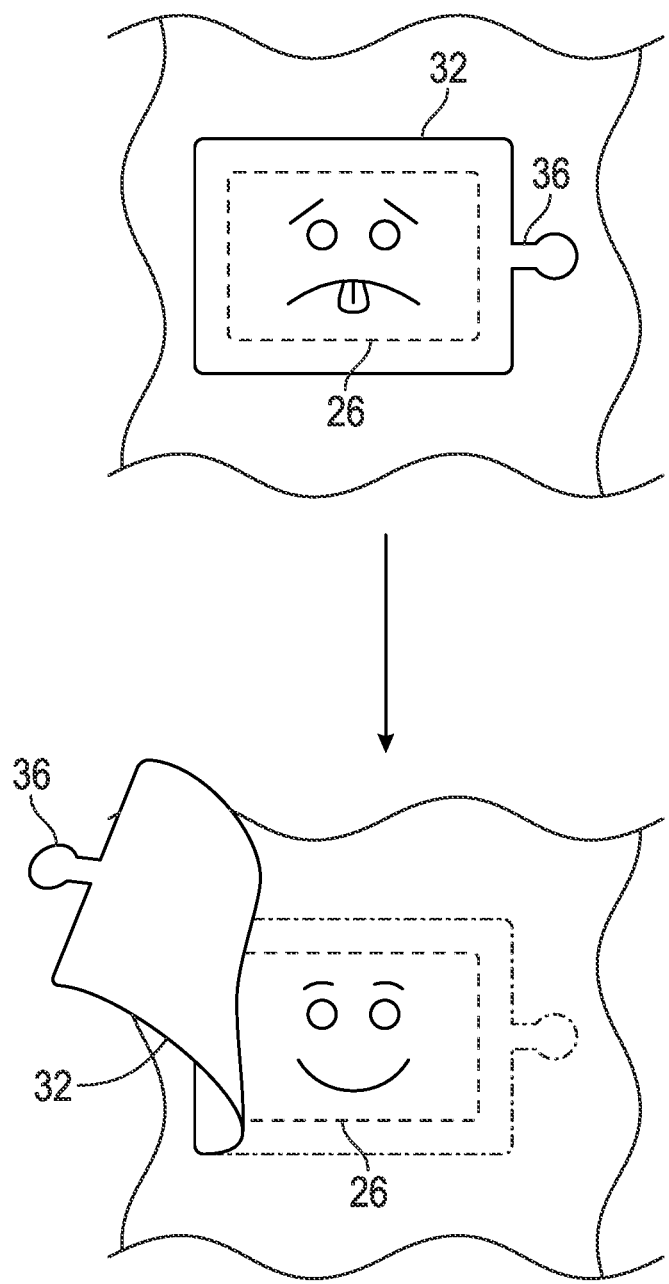
FIG. 5 is an enlarged plan view sequence of an additional embodiment of the invention.

FIG. 5 shows how a packet or flap 32 can be pulled manually, and can bear an indicia on the outside and the inside. The outside may indicate that pulling and smelling will lead to relief in words or images. Inside may be an image that reinforces the benefits. Further psychological reinforcement may be printed on the product or packaging remind the user of the benefits of the aroma, and its effectiveness at avoiding vomiting in a certain percentage of cases.

The procedure for use involves the user being provided with the kit, pouch, or product. The bag is removed from the pouch, and extended or unfolded to its full length. The aroma packet is unsealed by tearing, or by the act of extending the bag. The user than sniffs or breathes from the bag to smell the aroma, and may experience relief from the nausea so that equilibrium may be restored, or to delay vomiting until the user may get to a private bathroom, safely out of a vehicle, or comfortable away from fellow air passengers. Meanwhile, the bag is immediately ready while dispensing the aroma therapy, and the bag need only be shifted from the nose to cover the mouth, or may cover both.

The released aroma also indicates to a care provider or service personnel that the bag has been used, even if it did not need to receive vomit. This avoids unwanted reuse of an empty bag that has been in contact with one person who may have a communicable disease to a subsequent patient or user.

I claim:

1. A nausea-relieving vomit facility comprising:
a receptacle defining a storage chamber;
the receptacle having an opening providing access to the storage chamber;
a nausea-relief element including a fluid contained within an impermeable enclosure
the impermeable enclosure attached to the receptacle;
the impermeable enclosure being fluidically and aromatically isolated from the storage chamber when the impermeable enclosure is unopened;
the storage chamber being accessible for use by way of the opening independently of whether the impermeable enclosure is opened or unopened;
wherein the nausea-relief element is a sealed packet having a manual release facility;
wherein the manual release facility includes a tag connected to a portion of the receptacle away from the nausea-relief element, and
wherein the receptacle has a collapsed condition configured for compact storage and an expanded condition configured for receiving vomit; and
wherein the tag is operably connected to the receptacle at two different positions that are proximate in the collapsed condition and spaced apart in the expanded condition, such that the tag opens the nausea-relieving vomit facility in response to moving the receptacle from the collapsed condition to the expanded condition.

2. The facility of claim 1 wherein the storage chamber has an interior surface, and the nausea-relief element is attached to the interior surface.

3. The facility of claim 1 wherein the entire receptacle defines the storage chamber.

4. The facility of claim 1 wherein the receptacle is a flexible bag.

5. The facility of claim 1 wherein the nausea-relief element includes an aromatic treatment for nausea.

6. The facility of claim 1 wherein the nausea-relief element is away from the opening.

7. The facility of claim 1 wherein the impermeable enclosure is a packet having an opening facility.

8. The facility of claim 1 wherein the nausea-relief element includes an essential oil.

9. The facility of claim 1 wherein the nausea-relief element includes an aromatic compound selected from a group of aromatic compounds including Ginger, Lavender, Roman chamomile, Cardamom, Coriander, Fennel, Nutmeg, Melissa, Aniseed, Star anise, Bergamot, Black pepper, Spearmint, and Geranium.

10. The facility of claim 1 wherein the nausea-relief element includes mint oil.

11. The facility of claim 1 wherein the receptacle is a flexible material impermeable to aromas.

12. The facility of claim 11 wherein the flexible material is selected from a group including paper, fabric, foil and plastic.

13. The facility of claim 1 wherein the nausea-relief element includes an absorbent carrier element.

14. The facility of claim 1 wherein the manual release facility is selected from a group including pull tabs, pre-scored edges, tear strings, and tear tapes.

15. The facility of claim 1 wherein the nausea-relief element is contained within the receptacle when the opening of the receptacle is occluded by a user's face, such that an aroma from the relief element is maintained for inhalation by the user.

16. The facility of claim 1 wherein the receptacle has a bottom surface, and the nausea-relief element is attached to the bottom surface.

* * * * *